United States Patent
Riordan

(10) Patent No.: US 7,087,553 B2
(45) Date of Patent: Aug. 8, 2006

(54) SOIL FUMIGANT, HERBICIDE, LARVACIDE, OVACIDE AND FUNGICIDE

(76) Inventor: Fredricka Riordan, 403-4250, San Ramón de Alajuela (CR)

( * ) Notice: Subject to any disclaimer, the term of this patent is extended or adjusted under 35 U.S.C. 154(b) by 16 days.

(21) Appl. No.: 10/359,925

(22) Filed: Feb. 5, 2003

(65) Prior Publication Data

US 2004/0033900 A1    Feb. 19, 2004

Related U.S. Application Data

(60) Provisional application No. 60/421,237, filed on Oct. 25, 2002, provisional application No. 60/354,902, filed on Feb. 5, 2002.

(51) Int. Cl.
| | |
|---|---|
| *A01N 59/26* | (2006.01) |
| *A01N 47/46* | (2006.01) |
| *A01N 43/647* | (2006.01) |
| *A01P 3/00* | (2006.01) |
| *A01P 13/00* | (2006.01) |

(52) U.S. Cl. .................. 504/127; 504/139; 504/141; 504/308; 514/382; 514/514; 424/601; 424/605

(58) Field of Classification Search ............... 504/127, 504/139, 141, 308; 514/514, 382; 424/601, 424/605

See application file for complete search history.

(56) References Cited

U.S. PATENT DOCUMENTS

| | | |
|---|---|---|
| 6,051,233 A | 4/2000 | Champon |
| 6,107,319 A | 8/2000 | Long et al. |
| 6,207,705 B1 | 3/2001 | Coats et al. |
| 6,458,747 B1 * | 10/2002 | Kulik ................ 504/140 |

* cited by examiner

*Primary Examiner*—S. Mark Clardy
(74) *Attorney, Agent, or Firm*—Pandiscio & Pandiscio

(57) ABSTRACT

A treatment for eliminating unwanted organisms in agriculture, the treatment comprising a first component comprising allyl isothiocyanate emulsified in water, and a second component comprising a solution of phosphorus and water.

47 Claims, No Drawings

SOIL FUMIGANT, HERBICIDE, LARVACIDE, OVACIDE AND FUNGICIDE

REFERENCE TO PRIOR PENDING PATENT APPLICATIONS

This patent application claims benefit of:

(1) pending prior U.S. Provisional Patent Application Ser. No. 60/354,902, filed Feb. 5, 2002 by Fredricka Riordan for SOIL FUMIGANT AND/OR FOLIAR HERBICIDE COMPRISING THE COMBINED USE OF MUSTARD OIL AND PHOSPHORUS; and (2) pending prior U.S. Provisional Patent Application Ser. No. 60/421,237, filed Oct. 25, 2002 by Fredricka Riordan for SOIL FUMIGANT AND/OR FOLIAR HERBICIDE COMPRISING THE COMBINED USE OF MUSTARD OIL AND PHOSPHORUS.

FIELD OF THE INVENTION

This invention relates to agricultural products in general, and more particularly to soil fumigants, topical herbicides, larvacides, ovacides and fungicides.

BACKGROUND OF THE INVENTION

In the agricultural industry, it is frequently necessary or desirable to treat the soil with a soil fumigant and/or an herbicide. Soil fumigants are generally designed to sterilize the soil by (1) killing harmful organisms such as nematodes, fungi, bacteria, etc. and/or (2) provoking necrosis in plant tissue to prevent the rapid re-growth of weeds. Topical herbicides are generally designed to eradicate weeds after they have germinated.

Currently, the most effective substance for such a soil fumigant is methyl bromide. However, methyl bromide can be harmful to the nervous system and the respiratory system, and causes depletion of the earth's ozone layer. Methyl bromide is currently being phased out under the so-called Montreal Protocol. The world deadline for total elimination is 2015.

Approximately forty percent of the foliar herbicide used worldwide is paraquat. Paraquat can be fatal if inhaled or if it is absorbed through the skin.

In the agricultural industry, it is also frequently necessary or desirable to control insects and fungi on foliar surfaces/foliage with an insecticide or fungicide. Delivery is generally effected by terrestrial applicators and/or aerial applicators employing conventional flow or fine droplet dispersion.

Currently, the most preferred substances for insect and fungi control are the carbamates. Many carbamates must generally be applied weekly, but their low price can theoretically offset labor rates, whereby to maintain a low total investment in controlling insects and fungi. However, the side effects of their use are now generally acknowledged to affect the health and productivity of the agricultural workers. These side effects include nausea, cramps, diarrheas and flu-like symptoms in agricultural workers. The reduced worker productivity, and the accompanying increased healthcare costs, can make agriculture only marginally profitable in emerging economies. Many carbamate compounds are now under review by the EPA.

Novel Soil Fumigant

The present invention provides a novel soil fumigant through the combined use of mustard oil and a phosphorus source.

In accordance with the present invention, natural or synthetic mustard oil (allyl isothiocyanate, CAS 57-06-7, at a purity of approximately 85% to approximately 98%) is emulsified in water. Preferably the mustard oil is emulsified using a non-ionic detergent such as a polymer of ethylene oxide and nonylphenol (e.g., type Antarox CAS 9016-45-9 or NP-7 CAS 26027-38-3).

This emulsion is then applied to the soil through a conventional irrigation system, e.g., a drip or drench irrigation system, or topical spray drench. This emulsion is applied either beneath plastic tarps (drip) or the tarps are applied subsequent to the application (drench irrigation or topical spray drench).

Approximately two to three days after applying the emulsion, a solution of phosphorus (e.g., phosphoric acid, $H_3PO_4$, CAS 7664-38-2, at a concentration of 85%) and water is applied to the soil. This is preferably done using the same irrigation method and system used to apply the emulsion. The tarps remain in place (drip) or are replaced after the application (drench). In the soil, the phosphoric solution reacts with the chemicals introduced by the aforementioned emulsion, thereby providing an effective soil fumigant, which is substantially devoid of the disadvantages associated with methyl bromide. The mode of action is currently believed to be the corrosive process that occurs when the phosphorus and cyanide (naturally occurring in allyl isothiocyanate) are simultaneously present. This corrosive action expends oxygen; the oxygen in the soil is depleted, thereby killing the microorganisms and plant tissue.

The phosphoric solution can also be formed using components other than phosphoric acid, $H_3PO_4$, CAS 7664-38-2. By way of example but not limitation, the phosphoric solution can be formed by using components such as $NH_4H_2PO_4$ (NPK 12-60-0) CAS-7722-76 at a concentration approximately 45% to approximately 85%, a fertilizer rich in phosphorus (in the form of phosphate), $NOP_2O_5K_2O$ (NPK 10-30-10) at a concentration of approximately 30%, or $P_4O_5$ at a concentration of approximately 45%.

Approximately 8–10 days after applying the phosphorus solution, planting is effected.

In a preferred form of the invention, subsequent fertilization proportions consider the prior application of the phosphorus source described in this invention.

EXAMPLE 1

12 grams of mustard oil (allyl isothiocyanate, CAS 57-06-7, at a purity of approximately 85% to approximately 98%) is mixed with 300 liters of water at a temperature of approximately 25° C. This mixture is then emulsified by adding 300–600 grams of Antarox CAS 9016-45-9 or NP-7 CAS 26027-38-3, sufficient to achieve a satisfactory emulsion, at a temperature of approximately 25° C. The emulsion is then spread on 90 square meters of soil using a drip or drench irrigation system. Two to three days after applying the emulsion, a mixture of a phosphorus source and water (e.g., 815 grams of phosphoric acid $H_3PO_4$, CAS 7664-38-2, at a concentration of approximately 85%) in 500 liters of water, or 7500 grams of $NH_4H_2PO_4$ (NPK 12-60-0) CAS - 7722-76, at a concentration approximately 45% to approximately 85%, a fertilizer rich in phosphorus in the form of phosphate, in 500 liters of water) is applied to the soil. The tarps remain in place (drip) or are replaced after the application (drench) Planting is effected 8–10 days later. In a preferred form of the invention, subsequent fertilization proportions consider the prior application of the phosphorus source described in this invention.

Novel Herbicide

The present invention also provides a novel herbicide through the combined use of mustard oil and phosphorus or compounds derived from phosphorus.

In accordance with the present invention, natural or synthetic mustard oil (allyl isothiocyanate, CAS 57-06-7, at a purity of approximately 85% to approximately 98%), is emulsified in water. Preferably the mustard oil is emulsified using a non-ionic detergent such as a polymer of ethylene oxide and nonylphenol (e.g., Antarox CAS 9016-45-9 or NP-7 CAS 26027-38-3). The mixture is then applied directly to the soil at the root level. A solution of phosphorus source (e.g., phosphoric acid, $H_3PO_4$, CAS 7664-38-2, at a concentration of 85%) can be mixed with the emulsion or subsequently applied to the same root area as a spray drench to induce the desired necrosis. It has been found that the mixture acts as an excellent herbicide that is substantially devoid of the disadvantages associated with paraquat.

The phosphorus solution can also be formed using components other than phosphoric acid, $H_3PO_4$, CAS 7664-38-2. By way of example but not limitation, the phosphorus solution can be formed by using components such as $NH_4H_2PO_4$ (NPK 12-60-0) CAS 14265-44-2 at a concentration approximately 45% to approximately 85%, a fertilizer rich in phosphorus (in the form of phosphate), or $NOP_2O_5K_2O$ (NPK 10-30-10) at a concentration of approximately 30%, or $P_4O_5$ at a concentration of approximately 45%.

The phosphoric solution can also be formed using components other than phosphoric acid, $H_3PO_4$, CAS 7664-38-2 at an 85% concentration. By way of example but not limitation, the phosphoric solution can be formed by using components such as Ammonium Phosphate Monobasic CAS 7722-76-1, $NH_4H_2PO_4$ (commercial formula NPK 12-60-0), approximately 45% to approximately 85% concentration, a fertilizer rich in phosphorus (in the form of phosphate), the mixture $NOP_2O_5$—$K_2O$(commercial formula NPK 10-30-10) at approximately 45% to approximately 85% concentration, or pentoxide $P_4O_5$ CAS 1314-56-3 at approximately 45% concentration.

The mode of action is currently believed to be the corrosive action of the phosphorus in contact with the allyl isothiocyanate. The corrosive action immediately induces necrosis and desiccation in the porous root tissue, killing the undesired growth.

In a preferred form of the invention, subsequent fertilization proportions consider the prior application of the phosphorus source described in this invention.

EXAMPLE 2

40 grams of mustard oil (allyl isothiocyanate, CAS 57-06-7, at a purity of approximately 85% to approximately 98%) are mixed with 170 liters of water at a temperature of approximately 25° C. This mixture is then emulsified by adding 170 grams of Antarox CAS 9016-45-9 or NP-7 CAS 26027-38-3 at a temperature of approximately 25° C. 1385 grams of phosphoric acid ($H_3PO_4$, CAS 7664-38-2 at a concentration of approximately 85%) is then added to the emulsion. The mixture is then applied as a spray drench to the soil to induce the desired necrosis. In a preferred form of the invention, subsequent fertilization proportions consider the prior application of phosphorus source described in this invention.

Novel Larvacide, Ovacide And Fungicide

The present invention also provides a novel insecticide (through the control of insect larva and insect ova) and fungicide (through the control of fungi in its latent as well as active stages) which is realized through the combined use of mustard oil and phosphorus or compounds derived from phosphorus.

EXAMPLE 3

18 grams of mustard oil (allyl isothiocyanate, CAS 57-06-7, at a purity of approximately 85% to approximately 98%) is mixed with 400 liters of water at a temperature of approximately 25° C. This mixture is then emulsified by adding 400–1200 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphorus source and water (e.g., 815 grams of phosphoric acid, $H_3PO_4$, CAS 7664-38-2 at a concentration of approximately 45% to approximately 85%), in 500 liters of water, or 7500 grams of $NH_4H_2PO_4$ (NPK 12-60-0) CAS 14265-44-2 at a concentration approximately 45% to approximately 85%, to a fertilizer rich in phosphorus in the form of phosphate, in 500 liters of water) can be applied to the leaves. In a preferred form of the invention, the subsequent application of phosphorus conforms to the norms of the foliar fertilization cycle indicated for the specific crop being cultivated.

EXAMPLE 4

68 grams of mustard oil (allyl isothiocyanate, CAS 57-06-7, at a purity of approximately 85% to approximately 98%) are mixed with 40 liters of water at a temperature of approximately 25° C. This mixture is then emulsified by adding 300–900 grams of Antarox CAS 9016-45-9 or NP-7 CAS 26027-38-3 sufficient to achieve an emulsion at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Three days after applying the emulsion, a mixture of a phosphorus source and water (e.g., 815 grams of phosphoric acid, $H_3PO_4$, CAS 7664-38-2, at a concentration of approximately 45% to approximately 85%, in 40 liters of water) can be applied in the same manner. In a preferred form of the invention, the subsequent application of phosphorus conforms to the norms of the foliar fertilization cycle indicated for the specific crop being cultivated.

EXAMPLE 5

9 grams of mustard oil (allyl isothiocyanate, CAS 57-06-7, at a purity of approximately 85% to approximately 98%) are mixed with 200 liters of water at a temperature of approximately 25° C. This mixture is then emulsified by adding 200–600 grams of Antarox CAS 9016-45-9 or NP-7CAS 26027-38-3, sufficient to achieve an emulsion, at a temperature of approximately 25° C. The emulsion is then sprayed on a 500 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphoric source and water (e.g., 815 grams of phosphoric acid, $H_3PO_4$, CAS 7664-38-2 in 500 liters of water, at a concentration of approximately 45% to approximately 85%, or 750 grams of $NH_4H_2PO_4$ (NPK 12-60-0) CAS 14265-44-2 at a concentration approximately 45% to approximately 85%, a fertilizer rich in phosphorus in the form of phosphate, in 500 liters of water) can be applied to the leaves. In a preferred form of the invention, the subsequent application of phosphorus conforms to the norms of the foliar fertilization cycle indicated for the specific crop being cultivated.

Terpene

In a preferred form of the invention, the allyl isothiocyanate is diluted by a terpene. A preferred form of terpene is citric oil (D-Limonene or (R)-1-methyl-4-(1-methylethenyl) cyclohexene), CAS 5989-27-5, at a purity of approximately 77% to approximately 96%. Citric oil is believed to have an enhancing effect: (i) due to its low density and viscosity and its known qualities as a solvent, it facilitates the dispersion of the allyl isothiocyanate and its penetration of the interstices of the soil, plant matter, foliage and the cuticle of the leaves to be treated; (ii) when in contact with a phosphorus source, e.g. phosphoric acid, it breaks the surface tension of the phosphorus source and facilitates its dispersion in the soil; (iii) the terpene itself has some insecticidal, larvacidal, fungicidal and bactericidal properties; and (iv) the preferred form of terpene, citric oil, may react with water in the presence of hydrogen atoms released by $H_3PO_4$, the $H^+$, or from other acids which may be present, to yield α-terpineol CAS 8000-41-7—and since α-terpineol CAS 8000-41-7 is incompatible with oxidizing agents, the dilution of the allyl isothiocyanate by citric oil may enhance the corrosive action (depletion of oxygen) of allyl isothiocyanate in the presence of a phosphorus source.

EXAMPLE 1A 12 grams of mustard oil (allyl isothiocyanate, CAS 57-06-7, at a purity of approximately 85% to approximately 98%) and 2500 grams of citric oil (D-Limonene or (R)-1-methyl-4-(1-methylethelyn) cyclohexene, CAS 5989-27-5, at a purity of approximately 77% to approximately 96%) are mixed with 300 liters of water at a temperature of approximately 25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then spread on 90 square meters of soil using a drip or drench irrigation system. Two to three days after applying the emulsion, a mixture of a phosphoric source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76-1 at a concentration approximately 45% to approximately 85%, a fertilizer rich in phosphorus in the form of phosphate, in 500 liters of water) is applied to the soil. The tarps remain in place (drip) or are replaced after the application (drench). Eight to ten days later planting is effected. In a preferred form of the invention, subsequent fertilization proportions consider the prior application of the phosphorus source described in this invention.

EXAMPLE 2A 40 grams of mustard oil (allyl isothiocyanate, CAS 57-06-7, at a purity of approximately 85% to approximately 98%) and 2500 grams of citric oil (D-Limonene or (R)-1-methyl-4-(1-methylethelyn) cyclohexene, CAS 5989-27-5, at a purity of approximately 77% to approximately 96%) are mixed with 170 liters of water at a temperature of approximately 25° C. This mixture is then emulsified by adding 170–510 grams of Antarox CAS 9016-45-9 or NP-7 CAS 26027-38-3, sufficient to achieve an emulsion, at a temperature of approximately 25° C. 1385 grams of phosphoric acid, $H_3PO_4$, CAS 7664-38-2, at a concentration of approximately 45% to approximately 85%, is then added to the emulsion. The mixture is then applied as spray drenches to the soil to induce the desired necrosis. In a preferred form of the invention, subsequent fertilization proportions consider the prior application of the phosphorus source described in this invention.

EXAMPLE 3A 18 grams of mustard oil (allyl isothiocyanate, CAS 57-06-7, at a purity of approximately 85% to approximately 98%) and 400 grams of citric oil (D-Limonene or (R)-1-methyl-4-(1-methylethelyn) cyclohexene, CAS 5989-27-5, at a purity of approximately 7% to approximately 96%) are mixed with 400 liters of water at a temperature of approximately 25° C. This mixture is then emulsified by adding 400–1200 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76-1 at a concentration approximately 45% to approximately 85%, a fertilizer rich in phosphorus in the form of phosphate, in 500 liters of water) can be applied to the leaves. In this preferred form of the invention, the subsequent application of phosphorus conforms to the norms of the foliar fertilization cycle indicated for the specific crop being cultivated.

EXAMPLE 4A 68 grams of mustard oil (allyl isothiocyanate, CAS 57-06-7, at a purity of approximately 85% to approximately 98%) and 1000 grams of citric oil (D-Limonene or (R)-1-methyl-4-(1-methylethelyn) cyclohexene, CAS 5989-27-5, at a purity of approximately 77% to approximately 96%) are mixed with 40 liters of water at a temperature of approximately 25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Three days after applying the emulsion, a mixture of a phosphorus source and water (e.g., 815 grams of phosphoric acid, $H_3PO_4$, CAS 7664-38-2, at a concentration of approximately 45% to approximately 85%, in 40 liters of water) can be applied in the same manner. In a preferred form of the invention, the subsequent application of phosphorus conforms to the norms of the foliar fertilization cycle indicated for the specific crop being cultivated.

EXAMPLE 5A 9 grams of mustard oil (allyl isothiocyanate, CAS 57-06-7, at a purity of approximately 85% to approximately 98%) and 200 grams of citric oil (D-Limonene or (R)-1-methyl-4-(1-methylethelyn) cyclohexene, CAS 5989-27-5, at a purity of approximately 77% to approximately 96%) are mixed with 200 liters of water at a temperature of approximately 25° C. This mixture is then emulsified by adding 400–1200 grams of Antarox CAS 9016-45-9 or NP-7 CAS 26027-38-3, sufficient to achieve an emulsion, at a temperature of approximately 25° C. The emulsion is then sprayed on a 500 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphorus source and water (e.g., 815 grams of phosphoric acid, $H_3PO_4$, CAS 7664-38-2, mat a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) can be applied to the leaves. In a preferred form of the invention, the subsequent application of phosphorus conforms with the norms of the foliar fertilization cycle indicated for the specific crop being cultivated.

Triazoles

In accordance with a still further aspect of the present invention, the combination of allyl isothiocyanate and phosphorus can be further enhanced by adding a source that contains the triazole structure, $C_2H_3N_3$ (1,2,4 1 substituted) (CAS 288-88-0), at a concentration of approximately 2% to approximately 25%, to the allyl isothiocyanate. A source containing the triazole structure is believed to have an enhancing effect in combination with both allyl isothiocyanate and phosphorous as a fumigant and foliar herbicide: its structure is known to (i) act as a sterol biosynthesis inhibitor, stopping the production of ergosterol, which many pathogens produce in order to sustain their growth, when used as a fungicide, and (ii) induce chlorosis and death when used in higher doses as a foliar application. The triazole structure generally cannot kill fungus, but it enhances the fungicidal action of the invention by limiting further growth of the fungi in the interim before the full corrosive action of the allyl and the phosphorous described in this invention can kill all of the pathogens in the soil.

In foliar applications, delivered by aerial or terrestrial applicators, a source containing the triazole structure generally cannot kill fungus, but it enhances the fungicidal action of the invention by limiting further growth of any fungi which may be present while the allyl isothiocyanate kills fungi (in both the active and latent stages).

In one preferred form of the invention, the triazole source, ($C_2H_3N_3$ (1,2,4 1 substituted) (CAS 288-88-0), at a concentration of approximately 2% to approximately 98% of active ingredients), may comprise Rally (commercial name): alpha-Butyl-alpha-(4-chlorophenyl)-1H-1,2,4-triazole-1-propanenitrile; Tilt (commercial name): 1-[[2-(2,4-dichlorophenyl)-4-propyl-1,3-dioxolan-2-yl]methyl]-1H-1,2,4-triazole; Caramba (commercial name): (1RS,5RS :1RS,5 RS)-5-(4-Clorobencil)-2,2Dimetil-1(1H-1,2,4-Triazole-1-Imetil); Punch (commercial name): 1-((bis(4-fluorophenyl) methylsilyl)methyl)-1H-1,2,4-triazole.

EXAMPLE 1B 12 grams of mustard oil (allyl isothiocyanate, CAS 57-06-7, at a purity of approximately 85% to approximately 98%) and 250 grams of the triazole source, ($C_2H_3N_3$ (1,2,4 1 substituted) (CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba(commercial name): (1RS,5RS: 1RS,5 RS)-5-(4-Clorobencil)-2,2Dimetil-1-(1H-1,2,4-Triazole-1-Imetil); Punch (commercial name): 1-((bis (4-fluorophenyl)methylsilyl)methyl)-1H-1,2,4-Triazole) are mixed with 300 liters of water at a temperature of approximately 25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then spread on 90 square meters of soil using a drip or drench irrigation system. Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) is applied to the soil. The tarps remain in place (drip) or are replaced after the application (drench). Eight to ten days later planting is effected. In a preferred form of the invention, subsequent fertilization proportions consider the prior application of the phosphorus source described in this invention.

EXAMPLE 2B 40 grams of mustard oil (allyl isothiocyanate, CAS 57-06-7, at a purity of approximately 85% to approximately 98%) and 800 grams of the triazole source, ($C_2H_3N_3$ (1,2,4 1 substituted) (CAS 288-88-0), at a concentration of approximately 2% to approximately 98% of active ingredients), (Rally (commercial name): alpha-Butyl-alpha-(4-chlorophenyl)-1H-1,2,4-triazole-1-propanenitrile, Tilt (commercial name)::1-[[2-(2,4-dichlorophenyl)-4-propyl-1,3-dioxolan-2-yl]methyl]-1H 1,2,4-triazole; Caramba (commercial name):: (1RS,5RS: 1RS,5RS)-5-(4-Clorobencil)-2,2Dimetil-1-(1H-1,2,4-Triazole-1-Imetil); Punch (commercial name):: 1-((bis(4-fluorophenyl)methylsilyl)methyl)-1H-1,2,4-triazole) are mixed with 170 liters of water at a temperature of approximately 25° C. This mixture is then emulsified by adding 170–510 grams of Antarox CAS 9016-45-9 or NP-7 CAS 26027-38-3, sufficient to achieve an emulsion, at a temperature of approximately 25° C. 1385 grams of phosphoric acid, $H_3PO_4$, CAS 7664-38-2, at a concentration of approximately 45% to approximately 85%, is then added to the emulsion. The mixture is then applied as a spray drench to the soil to induce the desired necrosis. In a preferred form of the invention, subsequent fertilization proportions consider the prior application of the phosphorus source described in this invention.

EXAMPLE 3B 18 grams of mustard oil (allyl isothiocyanate, CAS 57-06-7, at a purity of approximately 85% to approximately 98%), and 540 grams of the triazole source, ($C_2H_3N_3$ (1,2,4 1 substituted) (CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba(commercial name): (1RS,5RS: 1RS, 5RS)-5-(4-Clorobencil)-2,2 Dimetil-1-(1H-1,2,4-Triazole-1-Imetil); Punch (commercial name): 1-((bis(4-fluorophenyl)methylsilyl)methyl)-1H-1,2,4-triazole), are mixed with 400 liters of water at a temperature of approximately 25° C. This mixture is then emulsified by adding 400–1200 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76 at a concentration approximately 45% to approximately 85%, a fertilizer rich in phosphorus in the form of phosphate, in 500 liters of water) can be applied to the leaves. In a preferred form of the invention, the subsequent application of phosphorus conforms with the norms of the foliar fertilization cycle indicated for the specific crop being cultivated.

EXAMPLE 4B 68 grams of mustard oil (allyl isothiocyanate, CAS 57-06-7, at a purity of approximately 85% to approximately 98%) is mixed with 1500 grams of the triazole source, ($C_2H_3N_3$ (1,2,4 1 substituted)(CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4dichlorophenyl)-4-propyl-1,3-dioxolan-2-yl]methyl]-1H-1,2,4-triazole; Caramba(commercial name): (1RS,5RS: 1RS,5RS)-5-(4-Clorobencil)-2,2Dimetil-1-(1H-1,2,4-Triazole-1-Imetil); Punch (commercial name): 1-((bis(4-fluorophenyl)methylsilyl)methyl)-1H-1,2,4-triazole) and 40 liters of water at a temperature of approximately 25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Three days after applying the emulsion, a mixture of a phosphorus source and water (e.g., 815 grams of phosphoric acid, $H_3PO_4$, CAS 7664-38-2, at a concentration of approximately 45% to approximately 85%, in 40 liters of water) can be applied in the same manner. In a preferred form of the invention, the subsequent application of phosphorus conforms with the norms of the foliar fertilization cycle indicated for the specific crop being cultivated.

EXAMPLE 5B 9 grams of mustard oil (allyl isothiocyanate, CAS 57-06-7, at a purity of approximately 85% to approximately 98%) and 270 grams of the triazole source ($C_2H_3N_3$ (1,2,4 1 substituted) (CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba(commercial name): (1RS,5RS: 1RS,5RS)-5-(4-Clorobencil)-2,2Dimetil-1-(1H-1,2,4-Triazole-1-Imetil); Punch (commercial name): 1-((bis(4-fluorophenyl)methylsilyl)methyl)-1H-1,2,4-triazole) are mixed with 200 liters of water at a temperature of approximately 25° C. This mixture is then emulsified by adding 400–1200 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) can be applied to the leaves. In a preferred form of the invention, the subsequent application of phosphorus conforms to the norms of the foliar fertilization cycle indicated for the specific crop being cultivated.

Carbonates of Soda

In one particularly preferred form of the invention, the combination of allyl isothiocyanate and phosphorus can be further enhanced by adding a carbonate of soda to the allyl isothiocyanate.

Allyl isothiocyanate generally decomposes in the presence of acids, so it is desirable to stabilize the allyl isothiocyanate in order to prevent rapid or premature decomposition. In this context, water should be considered to be an acid. Therefore, the application medium, water, should be adjusted to prevent the decomposition of the allyl isothiocyanate in the soil or to prolong its active life on a foliar surface. Adding a carbonate of soda, e.g., $NA_2CO_3$ (sodium carbonate) or $NaHCO_3$ (bicarbonate of soda) prevents allyl isothiocyanate decomposition by raising the pH of the water to that of a basic media (also called an alkaline media). The hydrogen ions (hydronium) $H^+$ concentration is reduced, which minimizes any possible reaction between these positive hydrogen ions ($H^+$) and the negative charge ions, e.g., thiocyanade (–NCS) and/or its potential disassociated ions, cyanade ($CN^-$) and/or sulfur $S^{-2}$. Carbonates of soda also reduce both the acrid odor of the allyl isothiocyanate and reduce the sensation of burning, irritation and lacrimation that occurs when allyl isothiocyanate is in contact with the water present in all living tissue.

Allyl isothiocyanate generally decomposes in the presence of acids, so it is desirable to stabilize the allyl isothiocyanate in order to prolong its active life on a foliar surface.

EXAMPLE 1C 12 grams of mustard oil (allyl isothiocyanate, CAS 57-06-7, at a purity of approximately 85% to approximately 98%) and 75 grams of a carbonate of soda, i.e., $NA_2CO_3$ (sodium carbonate) or $NaHCO_3$ (bicarbonate of soda), are mixed with 300 liters of water at a temperature of approximately 25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then spread on 90 square meters of soil using a drip or drench irrigation system. Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) is applied to the soil. The tarps remain in place (drip) or are replaced after the application (drench). Eight to ten days later planting is effected. In a preferred form of the invention, subsequent fertilization proportions consider the prior application of the phosphorus source described in this invention.

EXAMPLE 2C 40 grams of mustard oil (allyl isothiocyanate, CAS 57-06-7, at a purity of approximately 85% to approximately 98%) and 45 grams of a carbonate of soda, i.e., $NA_2CO_3$ (sodium carbonate) or $NaHCO_3$ (bicarbonate of soda), are mixed with 170 liters of water at a temperature of approximately 25° C. This mixture is then emulsified by adding 170–510 grams of Antarox CAS 9016-45-9 or NP-7 CAS 26027-38-3, sufficient to achieve an emulsion, at a temperature of approximately 25° C. 1385 grams of phosphoric acid, $H_3PO_4$, CAS 7664-38-2, at a concentration of approximately 45% to approximately 85%, is then added to the emulsion. The mixture is then applied as a spray drench to the soil to induce the desired necrosis. In a preferred form of the invention, subsequent fertilization proportions consider the prior application of the phosphorus source described in this invention.

EXAMPLE 3C 18 grams of mustard oil (allyl isothiocyanate, CAS 57-06-7, at a purity of approximately 85% to approximately 98%) and 400 grams of a carbonate of soda i.e., $NA_2CO_3$ (sodium carbonate) or $NaHCO_3$ (bicarbonate of soda), are mixed with 400 liters of water at a temperature of approximately 25° C. This mixture is then emulsified by adding 400–1200 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages).

Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) can be applied to the foliage. In a preferred form of the invention, the subsequent application of phosphorus conforms to the norms of the foliar fertilization cycle indicated for the specific crop being cultivated.

EXAMPLE 4C 68 grams of mustard oil (allyl isothiocyanate, CAS 57-06-7, at a purity of approximately 85% to approximately 98%) and 400 grams of a carbonate of soda, i.e., $NA_2CO_3$ (sodium carbonate) or $NaHCO_3$ (bicarbonate of soda), are mixed with 40 liters of water at a temperature of approximately 25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Three days after applying the emulsion, a mixture of a phosphorus source and water (e.g., 815 grams of phosphoric acid, $H_3PO_4$, CAS 7664-38-2, at a concentration of approximately 45% to approximately 85%, in 40 liters of water) can be applied in the same manner. In a preferred form of the invention, the subsequent application of phosphorus conforms with the norms of the foliar fertilization cycle indicated for the specific crop being cultivated.

EXAMPLE 5C 9 grams of mustard oil (allyl isothiocyanate, CAS 57-06-7, at a purity of approximately 85% to approximately 98%) and 200 grams of a carbonate of soda, i.e., $NA_2CO_3$ (sodium carbonate) or $NaHCO_3$ (bicarbonate of soda), are mixed with 200 liters of water at a temperature of approximately 25° C. This mixture is then emulsified by adding 200–600 grams of Antarox CAS 9016-45-9 or NP-7 CAS 26027-38-3,sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Three days after applying the emulsion, a mixture of a phosphorus source and water (e.g., 815 grams of phosphoric acid, $H_3PO_4$, CAS 7664-38-2, at a concentration of approximately 45% to approximately 85%, in 40 liters of water) can be applied in the same manner. In a preferred form of the invention, the subsequent application of phosphorus conforms to the norms of the foliar fertilization cycle indicated for the specific crop being cultivated.

Terpene, Triazole and Carbonates of Soda

In accordance with a still further aspect of the present invention, in one particularly preferred form of the invention, the combination of allyl isothiocyanate and phosphorus can be further enhanced by adding a terpene, a triazole source and a carbonate of soda to the allyl isothiocyanate.

EXAMPLE 1D 12 grams of mustard oil (allyl isothiocyanate, CAS 57-06-7, at a purity of approximately 85% to approximately 98%), 2500 grams of citric oil (D-Limonene or (R)-1-methyl-4-(1-methylethelyn) cyclohexene, CAS 5989-27-5, at a purity of approximately 77% to approximately 96%), 250 grams of a triazole source ($C_2H_3N_3$ (1,2,4 1 substituted) (CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba(commercial name): (1RS,5RS: 1RS,5RS)-5-(4-Clorobencil)-2,2Dimetil-1-(1H-1,2,4-Triazole-1-Imetil); Punch (commercial name): 1-((bis(4-fluorophenyl)methylsilyl)methyl)-1H-1,2,4-triazole), and 300 grams of a carbonate of soda, i.e., $NA_2CO_3$ (sodium carbonate) or $NaHCO_3$ (bicarbonate of soda), are mixed with 300 liters of water at a temperature of approximately 25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then spread on 90 square meters of soil using a drip or drench irrigation system. Two to three days after applying the emulsion, a mixture of a phosphoric source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) is applied to the soil. The tarps remain in place (drip) or are replaced after the application (drench). Eight to ten days later planting is effected. In a preferred form of the invention, subsequent fertilization proportions consider the prior application of the phosphorus source described in this invention.

EXAMPLE 2D 40 grams of mustard oil (allyl isothiocyanate, CAS 57-06-7, at a purity of approximately 85% to approximately 98%), 2500 grams of citric oil (D-Limonene or (R)-1-methyl-4-(1-methylethelyn) cyclohexene, CAS 5989-27-5, at a purity of approximately 77% to approximately 96%), 800 grams of a triazole source ($C_2H_3N_3$ (1,2,4 1 substituted) (CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba(commercial name): (1RS,5RS: 1RS,5RS)-5-(4-Clorobencil)-2,2Dimetil-1(1-(1H-1,2,4-Triazole-1-Imetil); Punch (commercial name): 1-((bis(4-fluorophenyl)methylsilyl)methyl)-1H-1,2,4-triazole); and 45 grams of a carbonate of soda, i.e., $NA_2CO_3$ (sodium carbonate) or $NaHCO_3$ (bicarbonate of soda) are mixed with 170 liters of water at a temperature of approximately 25° C. This mixture is then emulsified by adding 170–510 grams of Antarox CAS 9016-45-9 or NP-7 CAS 26027-38-3, sufficient to achieve an emulsion, at a temperature of approximately 25° C. 1385 grams of phosphoric acid, $H_3PO_4$, CAS 7664-38-2, at a concentration of approximately 45% to approximately 85%, is then added to the emulsion. The mixture is then applied as a spray drench to the soil to induce the desired necrosis. In a preferred form of the invention, subsequent fertilization proportions consider the prior application of the phosphorus source described in this invention.

EXAMPLE 3D 18 grams of mustard oil (allyl isothiocyanate, CAS 57-06-7, at a purity of approximately 85% to approximately 98%), 400 grams of citric oil (D-Limonene or (R)-1-methyl-4-(1-methylethelyn) cyclohexene, CAS 5989-27-5, at a purity of approximately 77% to approximately 96%), 540 grams of a triazole source ($C_2H_3N_3$ (1,2,4 1 substituted) (CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba(commercial name): (1RS,5RS:1RS,5RS)-5-(4-Clorobencil)-2,2Dimetil-1-(1H-1,2,4-Triazole-1-Imetil); Punch (commercial name): 1-((bis(4-fluorophenyl) methylsilyl)methyl)-1H-1,2,4-triazole) and 400 grams of a carbonate of soda, i.e., $NA_2CO_3$ (sodium carbonate) or $NaHCO_3$ (bicarbonate of soda), are mixed with 400 liters of water at a temperature of approximately 25° C. This mixture is then emulsified by adding 400–1200 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) can be applied to the leaves. In a preferred form of the invention, the subsequent application of phosphorus is applied only within the norms of the foliar fertilization cycle indicated for the specific crop being cultivated.

EXAMPLE 4D 68 grams of mustard oil (allyl isothiocyanate, CAS 57-06-7, at a purity of approximately 85% to approximately 98%), 1000 grams of citric oil (D-Limonene or (R)-1-methyl-4-(1-methylethelyn) cyclohexene, CAS 5989-27-5, at a purity of approximately 77% to approximately 96%), 1500 grams of a triazole source ($C_2H_3N_3$ (1,2,4 1 substituted) (CAS 288-88-0), at a concentration of approximately 2% to approximately 98% of active ingredients (e.g. Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba(commercial name): (1RS,5RS: 1RS,5RS)-5(4-Clorobencil)-2,2Dimetil-1-(1H-(1,2,4-Triazole-1-Imetil); Punch (commercial name): 1-((bis(4-fluorophenyl)methylsilyl)methyl)-1H-1,2,4-triazole) and (400 grams of a carbonate of soda, i.e., $NA_2CO_3$ (sodium carbonate) or $NaHCO_3$ (bicarbonate of soda), are mixed with 40 liters of water at a temperature of approximately (25° C. This mixture is then emulsified by adding 300–900 grams of Antarox CAS 9016-45-9 or NP-7 CAS 26027-38-3, sufficient to achieve an emulsion, at a temperature of approximately 25° C. The emulsion is then sprayed on a 1000 square meter planted area. Delivery is effected by terrestrial applicators and/or aerial applicators employing conventional flow and/or fine droplet dispersion in order to kill insect larva, insect eggs and fungus (in active and latent stages). Three days after applying the emulsion, a mixture of a phosphorus source and water (e.g., 815 grams of phosphoric acid, $H_3PO_4$, CAS 7664-38-2, at a concentration of approximately 45% to approximately 85%, in 40 liters of water) can be applied in the same manner. In a preferred form of the invention, the subsequent application of phosphorus conforms with the norms of the foliar fertilization cycle indicated for the specific crop being cultivated.

EXAMPLE 5D 9 grams of mustard oil (allyl isothiocyanate, CAS 57-06-7, at a purity of approximately 85% to approximately 98%), 200 grams of citric oil (D-Limonene or (R)-1-methyl-4-(1-methylethelyn) cyclohexene, CAS 5989-27-5, at a purity of approximately 77% to approximately 96%), 270 grams of a triazole source ($C_2H_3N_3$ (1,2,4 1 substituted) (CAS 288-88-0), at a concentration of approximately 2% to approximately 98% of active ingredients (e.g., Rally (commercial name): alpha-Butyl-alpha-(4-chlorophenyl)-1H-1,2,4-triazole-1-propanenitrile, Tilt (commercial name): 1-[[2-(2,4-dichlorophenyl)-4-propyl-1,3-dioxolan-2-yl]methyl]-1H-1,2,4-triazole; Caramba (commercial name): (1RS,5RS: 1RS, 5RS)-5-(4-Clorobencil)-2,2Dimetil-1-(1H-1,2,4-Triazole-1-Imetil); Punch (commercial name): 1-((bis(4-fluorophenyl) methylsilyl)methyl)-1H-1,2,4-triazole) and 200 grams of a carbonate of soda, i.e., $NA_2CO_3$ (sodium carbonate) or $NaHCO_3$ (bicarbonate of soda), are mixed with 200 liters of water at a temperature of approximately 25° C. This mixture is then emulsified by adding 200–600 grams of Antarox CAS 9016-45-9 or NP-7 CAS 26027-38-3, sufficient to achieve an emulsion, at a temperature of approximately 25° C. The emulsion is then sprayed on a 500 square meter planted area. Delivery is effected by terrestrial applicators and/or aerial applicators employing conventional flow and/or fine droplet dispersion in order to kill insect larva, insect eggs and fungus (in active and latent stages). Two to three days after applying the emulsion, a mixture of a phosphorus source and water (e.g., 815 grams of phosphoric acid, $H_3PO_4$, CAS 7664-38-2, at a concentration of approximately 45% to approximately 85%, in 500 liters of water, or 750 grams of $NH_4H_2PO_4$, NPK 12-60-0, CAS-7722-76, at a concentration approximately 45% to approximately 85%, a fertilizer rich in phosphorus in the form of phosphate, in 500 liters of water) can be applied to the leaves. In a preferred form of the invention, the subsequent application of phosphorus conforms to the norms of the foliar fertilization cycle indicated for the specific crop being cultivated.

Further Details

Additional details regarding various preferred embodiments of the invention are set forth in the attached Appendices A, B and C.

Additional Modifications

It will be appreciated that many additional changes in the details, materials and steps, which have been herein described and illustrated in order to explain the nature of the invention, may be made by those skilled in the art within the principles and scope of the invention as expressed in the appended claims.

What is claimed is:

1. A method for eliminating unwanted organisms in agriculture, said method comprising:

applying a first component comprising allyl isothiocyanate emulsified in water to an agricultural area; and applying a second component comprising an aqueous solution of a phosphorus compound selected from a group consisting of phosphoric acid and fertilizer salts thereof to the agricultural area;

wherein said step of applying said second component occurs at one selected from a group consisting of (1) simultaneous with said step of applying said first component and (2) within a given time period subsequent to said step of applying said first component, and wherein said second component is applied to the agricultural area such that said phosphorus compound of said second component chemically interacts with said allyl isothiocyanate of said first component so as to create a corrosive reaction which eliminates unwanted organisms from the agricultural area.

2. A method according to claim 1 wherein said first component comprises allyl isothiocyanate emulsified in a non-ionic detergent.

3. A method according to claim 2 wherein said non-ionic detergent comprises a polymer of ethylene oxide and nonylphenol.

4. A method according to claim 1 wherein said second component comprises phosphoric acid and water.

5. A method according to claim 1 wherein said second component comprises $NH_4H_2PO_4$.

6. A method according to claim 1 wherein said second component comprises $NOP_2O_5K_2O$.

7. A method according to claim 1 wherein said second component comprises $P_4O_5$.

8. A method according to claim 1 wherein said second component is applied 2 to 3 days after said first component is applied.

9. A method according to claim 1 wherein said second component is applied simultaneously with said first component.

10. A method according to claim 1 wherein said first component further comprises a terpene.

11. A method according to claim 10 wherein said terpene is citric oil.

12. A method according to claim 1 wherein said first component further comprises a triazole.

13. A method according to claim 12 wherein said triazole comprises at least one chosen from the group consisting of: myclobutanil, propiconazole, metconazol and flusilazole, at a concentration of approximately 2% to approximately 98% of active ingredients.

14. A method according to claim 1 wherein said first component further comprises a carbonate of soda.

15. A method according to claim 14 wherein said carbonate of soda comprises $Na_2CO_3$.

16. A method according to claim 14 wherein said carbonate of soda comprises $NaHCO_3$.

17. A method according to claim 1 wherein said first component further comprises a terpene, a triazole and a carbonate of soda.

18. A method for eliminating unwanted organisms in agriculture, said method comprising:

applying a first component comprising allyl isothiocyanate emulsified in water to an agricultural area, said allyl isothiocyanate comprising between approximately 0.0040% and approximately 7.0% of said first component by weight; and applying a second component comprising an aqueous solution of a phosphorus compound selected from a group consisting of phosphoric acid and fertilizer salts thereof to the agricultural area;

wherein said step of applying said second component occurs at one selected from a group consisting of (1) simultaneous with said step of applying said first component and (2) within a given time period subsequent to said step of applying said first component, and wherein said second compound is applied to the agricultural area such that said phosphorus compound of said second component chemically interacts with said allyl isothiocyanate of said first component so as to create a corrosive reaction which eliminates unwanted organisms from the agricultural area, said phosphorus compound comprising between approximately 0.08% and approximately 10.0% of said second component by weight; and wherein said first component comprises between approximately 25% and approximately 75% of a total of said first component and said second component by weight.

19. A method according to claim 18 wherein said first component further comprises a terpene, said terpene comprising between approximately 0.001% and approximately 20% of said first component by weight.

20. A method according to claim 18 wherein said first component further comprises a triazole, said triazole comprising between approximately 0.01% and approximately 10% of said first component by weight.

21. A method according to claim 18 wherein said first component further comprises a carbonate of soda, said carbonate of soda comprising between approximately 0.01% and approximately 3.0% of said first component by weight.

22. A method for eliminating unwanted organisms in agriculture, said method comprising:
providing a first component comprising allyl isothiocyanate emulsified in water, and a second component comprising an aqueous solution of a phosphorus compound selected from a group consisting of phosphoric acid and fertilizer salts thereof; and
applying said first component and said second component to an agricultural area such that said allyl isothiocyanate of said first component chemically interacts with said phosphorus compound of said second component so as to create a corrosive reaction which eliminates unwanted organisms from the agricultural area.

23. A method for eliminating unwanted organisms in agriculture, said method comprising:
applying a first component comprising allyl isothiocyanate emulsified in water to an agricultural area; and
applying a second component comprising an aqueous solution of a phosphorus compound to the agricultural area;
wherein said step of applying said second component occurs at one selected from a group consisting of (1) simultaneous with said step of applying said first component and (2) within a given time period subsequent to said step of applying said first component, and wherein said second component is applied to the agricultural area such that said phosphorus compound of said second component chemically interacts with said allyl isothiocyanate of said first component so as to create a corrosive reaction which eliminates unwanted organisms from the agricultural area; and
wherein said second component comprises phosphoric acid and water.

24. A method for eliminating unwanted organisms in agriculture, said method comprising:
applying a first component comprising allyl isothiocyanate emulsified in water to an agricultural area; and
applying a second component comprising an aqueous solution of a phosphorus compound to the agricultural area;
wherein said step of applying said second component occurs at one selected from a group consisting of (1) simultaneous with said step of applying said first component and (2) within a given time period subsequent to said step of applying said first component, and wherein said second component is applied to the agricultural area such that said phosphorus compound of said second component chemically interacts with said allyl isothiocyanate of said first component so as to create a corrosive reaction which eliminates unwanted organisms from the agricultural area; and
wherein said second component comprises $NH_4H_2PO_4$.

25. A method for eliminating unwanted organisms in agriculture, said method comprising:
applying a first component comprising allyl isothiocyanate emulsified in water to an agricultural area; and
applying a second component comprising an aqueous solution of a phosphorus compound to the agricultural area;
wherein said step of applying said second component occurs at one selected from a group consisting of (1) simultaneous with said step of applying said first component and (2) within a given time period subsequent to said step of applying said first component, and wherein said second component is applied to the agricultural area such that said phosphorus compound of said second component chemically interacts with said allyl isothiocyanate of said first component so as to create a corrosive reaction which eliminates unwanted organisms from the agricultural area; and
wherein said second component comprises $NOP_2O_5K_2O$.

26. A method for eliminating unwanted organisms in agriculture, said method comprising:
applying a first component comprising allyl isothiocyanate emulsified in water to an agricultural area; and
applying a second component comprising an aqueous solution of a phosphorus compound to the agricultural area;
wherein said step of applying said second component occurs at one selected from a group consisting of (1) simultaneous with said step of applying said first component and (2) within a given time period subsequent to said step of applying said first component, and wherein said second component is applied to the agricultural area such that said phosphorus compound of said second component chemically interacts with said allyl isothiocyanate of said first component so as to create a corrosive reaction which eliminates unwanted organisms from the agricultural area; and
wherein said second component comprises $P_4O_5$.

27. A kit for eliminating unwanted organisms in agriculture, said kit comprising:
a first component comprising allyl isothiocyanate emulsified in water;
a second component comprising an aqueous solution of a phosphorus compound selected from a group consisting of phosphoric acid and fertilizer salts thereof; and
instructions wherein the end user is directed to apply the first component to an agricultural area, and simultaneous with the first application, or subsequent thereto, apply the second component to the agricultural area such that said phosphorus compound of said second component chemically interacts with said allyl isothiocyanate of said first component so as to create a corrosive reaction which eliminates unwanted organisms from the agricultural area.

28. A kit according to claim 27 wherein said first component comprises allyl isothiocyanate emulsified in a nonionic detergent.

29. A kit according to claim 28 wherein said nonionic detergent comprises a polymer of ethylene oxide and nonylphenol.

30. A kit according to claim 27 wherein said second component comprises phosphoric acid and water.

31. A kit according to claim 27 wherein said second component comprises $NH_4H_2PO_4$.

32. A kit according to claim 27 wherein said second component comprises $NOP_2O_5K_2O$.

33. A kit according to claim 27 wherein said second component comprises $P_4O_5$.

34. A kit according to claim 27 wherein said first component further comprises a terpene.

35. A kit according to claim 34 wherein said terpene is citric oil.

36. A composition kit according to claim 27 wherein said first component further comprises a triazole.

37. A composition kit according to claim 36 wherein said triazole comprises at least one chosen from the group consisting of: myclobutanil, propiconazole, metconazole and flusilazole, at a concentration of approximately 2% to approximately 98% of active ingredients.

38. A kit according to claim 27 wherein said first component further comprises a carbonate of soda.

39. A kit according to claim 38 wherein said carbonate of soda comprises $Na_2CO_3$.

40. A kit according to claim 38 wherein said carbonate of soda comprises $NaHCO_3$.

41. A kit according to claim 27 wherein said first component further comprises a terpene, a triazole and a carbonate of soda.

42. A kit for eliminating unwanted organisms in agriculture, said kit comprising:
a first component comprising allyl isothiocyanate emulsified in water, said allyl isothiocyanate comprising between approximately 0.0040% and approximately 7.0% of said first component by weight;
a second component comprising an aqueous solution of a phosphorus compound selected from a group consisting of phosphoric acid and fertilizer salts thereof; and
instructions wherein the end user is directed to apply the first component to an agricultural area, and simultaneous with the first application, or subsequent thereto, apply the second component to the agricultural area such that said phospohorus compound of said second component chemically interacts with said allyl isothiocyanate of said first component so as to create a corrosive reaction which eliminates unwanted organisms from the agricultural area, said phosphorus compound comprising between approximately 0.08% and approximately 10.0% of said second component by weight; and
said first component comprising between approximately 25% and approximately 75% of a total of said first component and said second component by weight.

43. A kit according to claim 42 wherein said first component further comprises a terpene, said terpene comprising between approximately 0.001% and approximately 20% of said first component by weight.

44. A kit according to claim 42 wherein said first component further comprises a triazole, said triazole comprising between approximately 0.01% and approximately 10% of said first component by weight.

45. A kit according to claim 42 wherein said first component further comprises a carbonate of soda, said carbonate of soda comprising between approximately 0.01% and approximately 3.0% of said first component by weight.

46. A kit for eliminating unwanted organisms in agriculture, said kit comprising:
a first component comprising allyl isothiocyanate emulsified in water, and a second component comprising an aqueous solution of a phosphorus compound selected from a group consisting of phosphoric acid and fertilizer salts thereof; and
instructions wherein the end user is directed to apply the first component and the second component to an agricultural area such that said allyl isothiocyanate of said first component chemically interacts with said phosphorus compound of said second component so as to create a corrosive reaction which eliminates unwanted organisms from said agricultural area.

47. A composition for eliminating unwanted organisms in agriculture, said composition comprising:
a first component comprising allyl isothiocyanate emulsified in water; and
a second component comprising an aqueous solution of a phosphorus compound selected from the group consisting of phosphoric acid and fertilizer salts thereof.

* * * * *